United States Patent [19]
Tatsumi et al.

[11] Patent Number: 5,843,746
[45] Date of Patent: Dec. 1, 1998

[54] BIOTINATED FIREFLY LUCIFERASE, A GENE FOR BIOTINATED FIREFLY LUCIFERASE, A RECOMBINANT DNA, A PROCESS FOR PRODUCING BIOTINATED LUCIFERASE AND A BIOLUMINESCENT ANALYSIS METHOD

[75] Inventors: Hiroki Tatsumi; Satoshi Fukuda; Mamoru Kikuchi; Yasuji Koyama, all of Noda, Japan

[73] Assignee: Kikkoman Corporation, Noda, Japan

[21] Appl. No.: 782,118

[22] Filed: Jan. 13, 1997

Related U.S. Application Data

[62] Division of Ser. No. 460,934, Jun. 5, 1995.

[30] Foreign Application Priority Data

Jul. 27, 1994 [JP] Japan .................................. 6-193798
Mar. 14, 1995 [JP] Japan .................................. 7-054625
Apr. 24, 1995 [JP] Japan .................................. 7-098857

[51] Int. Cl.$^6$ .......................... C12N 15/62; C12N 15/53; C12N 1/21; C12N 15/63
[52] U.S. Cl. ........................ 435/189; 536/23.2; 536/23.4; 435/320.1; 435/252.3; 435/252.33; 435/69.7; 435/71.2
[58] Field of Search .................................. 536/23.2, 23.4; 435/320.1, 189, 252.3, 252.33, 69.7, 71.2

[56] References Cited

U.S. PATENT DOCUMENTS 5,229,285   7/1993   Kajiyama et al. ....................... 435/189
5,252,466   10/1993  Cronan, Jr. .............................. 435/69.7

FOREIGN PATENT DOCUMENTS 141 581   5/1985   European Pat. Off. .

OTHER PUBLICATIONS

C.S. Thompson et al., "Chimeric Proteins Incorporating an In Vivo Biotinylation Domain", Protein Engineering 6 Suppl.: 70, 1993.

P.J. Schatz, "Use of Peptide Libraries to Map the Substrate Specificity of a Peptide Modifying Enzyme: A 13 Residue Consensus Peptide Specifies Biotinylation in *Escherichia coli*" Biotecnology 11(10): 1138–1143, Oct. 1993.

*Primary Examiner*—Rebecca E. Prouty
*Attorney, Agent, or Firm*—Oblon, Spivak, McClelland, Maier & Neustadt, P.C.

[57] ABSTRACT

The present invention relates to biotinated firefly luciferase comprising a biotinated peptide and firefly luciferase linked therein, biotinated firefly luciferase having a specific amino acid sequence, a biotinated firefly luciferase gene comprising a gene coding for a biotinated peptide and a firefly luciferase gene linked therein, a biotinated firefly luciferase gene comprising a biotinated peptide gene coding for a specific amino acid sequence and a firefly luciferase gene linked therein, a recombinant DNA comprising said biotinated firefly luciferase gene inserted into a vector DNA, a process for producing biotinated firefly luciferase comprising culturing a microorganism belonging to the genus Escherichia carrying said recombinant DNA and then recovering the resulting biotinated firefly luciferase from the culture, a bioluminescent analysis method comprising using said biotinated firefly luciferase, and a bioluminescent analysis method comprising quantifying a ligand by measuring a biotinated receptor by the use of said biotinated firefly luciferase.

According to the present invention, there are provided biotinated firefly luciferase, a biotinated firefly luciferase gene, a recombinant DNA, a process for producing biotinated firefly luciferase and a bioluminescent analysis method. The present invention enables the efficient production of biotinated firefly luciferase of uniform properties with the uniform structure of firefly luciferase in which one biotin molecule has been bound to a specific residue and whose activity is hardly lost by biotination and not lost even binding to streptoavidin or avidin, and the biotinated firefly luciferase of constant properties obtained in the present invention permits highly sensitive measurements in bioluminescent analysis as compared with the conventional chemically modified biotinated firefly luciferase so that the present invention is industrially extremely useful.

21 Claims, 2 Drawing Sheets

LIL; LUCIOLA LATERALIS LUCIFERASE cDNA, #84; BIOTINATED PEPTIDE #84 Ap; β-LACTAMASE GENE, lacP; β-GALACTOSIDASE PROMOTER, E; EcoRI, H; HindIII, Hp; HpaI, M; MunI, X; XhoI.

LIL; LUCIOLA LATERALIS LUCIFERASE cDNA, Ap; β-LACTAMASE GENE, lacP; β-GALACTOSIDASE PROMOTER, E; EcoRI, B; BamHI.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 13
        ( D ) OTHER INFORMATION: /product="Lys-13"
            / note= "Biotinylated by biotin holoenzyme synthetase"

( x i ) SEQUENCE DESCRIPTION: SEQ ID NO:1:

```
Met  Ala  Phe  Ser  Leu  Arg  Ser  Ile  Leu  Glu  Ala  Gln  Lys  Met  Glu  Leu
1              5                        10                       15

Arg  Asn  Thr  Pro  Gly  Gly  Ser
                20
```

(2) INFORMATION FOR SEQ ID NO:2:

(i) SEQUENCE CHARACTERISTICS:
    (A) LENGTH: 548 amino acids
    (B) TYPE: amino acid
    (C) STRANDEDNESS: single
    (D) TOPOLOGY: unknown (ii) MOLECULE TYPE: peptide (vi) ORIGINAL SOURCE:
    (A) ORGANISM: Luciola lateralis (xi) SEQUENCE DESCRIPTION: SEQ ID NO:2:

```
Met  Glu  Asn  Met  Glu  Asn  Asp  Glu  Asn  Ile  Val  Tyr  Gly  Pro  Glu  Pro
1              5                        10                       15

Phe  Tyr  Pro  Ile  Glu  Glu  Gly  Ser  Ala  Gly  Ala  Gln  Leu  Arg  Lys  Tyr
                20                      25                       30

Met  Asp  Arg  Tyr  Ala  Lys  Leu  Gly  Ala  Ile  Ala  Phe  Thr  Asn  Ala  Leu
              35                        40                       45

Thr  Gly  Val  Asp  Tyr  Thr  Tyr  Ala  Glu  Tyr  Leu  Glu  Lys  Ser  Cys  Cys
        50                        55                       60

Leu  Gly  Glu  Ala  Leu  Lys  Asn  Tyr  Gly  Leu  Val  Val  Asp  Gly  Arg  Ile
65                      70                       75                            80

Ala  Leu  Cys  Ser  Glu  Asn  Cys  Glu  Glu  Phe  Phe  Ile  Pro  Val  Leu  Ala
                    85                        90                       95

Gly  Leu  Phe  Ile  Gly  Val  Gly  Val  Ala  Pro  Thr  Asn  Glu  Ile  Tyr  Thr
                100                      105                      110

Leu  Arg  Glu  Leu  Val  His  Ser  Leu  Gly  Ile  Ser  Lys  Pro  Thr  Ile  Val
              115                      120                      125

Phe  Ser  Ser  Lys  Lys  Gly  Leu  Asp  Lys  Val  Ile  Thr  Val  Gln  Lys  Thr
          130                      135                      140

Val  Thr  Ala  Ile  Lys  Thr  Ile  Val  Ile  Leu  Asp  Ser  Lys  Val  Asp  Tyr
145                      150                      155                           160

Arg  Gly  Tyr  Gln  Ser  Met  Asp  Asn  Phe  Ile  Lys  Lys  Asn  Thr  Pro  Gln
                    165                      170                      175

Gly  Phe  Lys  Gly  Ser  Ser  Phe  Lys  Thr  Val  Glu  Val  Asn  Arg  Lys  Glu
                180                      185                      190

Gln  Val  Ala  Leu  Ile  Met  Asn  Ser  Ser  Gly  Ser  Thr  Gly  Leu  Pro  Lys
          195                      200                      205

Gly  Val  Gln  Leu  Thr  His  Glu  Asn  Leu  Val  Thr  Arg  Phe  Ser  His  Ala
     210                      215                      220

Arg  Asp  Pro  Ile  Tyr  Gly  Asn  Gln  Val  Ser  Pro  Gly  Thr  Ala  Ile  Leu
225                      230                      235                           240

Thr  Val  Val  Pro  Phe  His  His  Gly  Phe  Gly  Met  Phe  Thr  Thr  Leu  Gly
               245                      250                      255

Tyr  Leu  Thr  Cys  Gly  Phe  Arg  Ile  Val  Met  Leu  Thr  Lys  Phe  Asp  Glu
               260                      265                      270

Glu  Thr  Phe  Leu  Lys  Thr  Leu  Gln  Asp  Tyr  Lys  Cys  Ser  Ser  Val  Ile
               275                      280                      285

Leu  Val  Pro  Thr  Leu  Phe  Ala  Ile  Leu  Asn  Arg  Ser  Glu  Leu  Leu  Asp
               290                      295                      300
```

| | | | | | | | | | | | | | | | |
|---|---|---|---|---|---|---|---|---|---|---|---|---|---|---|---|
|Lys|Tyr|Asp|Leu|Ser|Asn|Leu|Val|Glu|Ile|Ala|Ser|Gly|Gly|Ala|Pro|
|305| | | | |310| | | |315| | | | | |320|
|Leu|Ser|Lys|Glu|Ile|Gly|Glu|Ala|Val|Ala|Arg|Arg|Phe|Asn|Leu|Pro|
| | | | |325| | | |330| | | | | |335| |
|Gly|Val|Arg|Gln|Gly|Tyr|Gly|Leu|Thr|Glu|Thr|Thr|Ser|Ala|Ile|Ile|
| | | |340| | | | |345| | | | |350| | |
|Ile|Thr|Pro|Glu|Gly|Asp|Asp|Lys|Pro|Gly|Ala|Ser|Gly|Lys|Val|Val|
| | |355| | | | |360| | | | |365| | | |
|Pro|Leu|Phe|Lys|Ala|Lys|Val|Ile|Asp|Leu|Asp|Thr|Lys|Lys|Thr|Leu|
| |370| | | | |375| | | | |380| | | | |
|Gly|Pro|Asn|Arg|Arg|Gly|Glu|Val|Cys|Val|Lys|Gly|Pro|Met|Leu|Met|
|385| | | | |390| | | | |395| | | | |400|
|Lys|Gly|Tyr|Val|Asp|Asn|Pro|Glu|Ala|Thr|Arg|Glu|Ile|Ile|Asp|Glu|
| | | | |405| | | | |410| | | | |415| |
|Glu|Gly|Trp|Leu|His|Thr|Gly|Asp|Ile|Gly|Tyr|Tyr|Asp|Glu|Glu|Lys|
| | | |420| | | | |425| | | | |430| | |
|His|Phe|Phe|Ile|Val|Asp|Arg|Leu|Lys|Ser|Leu|Ile|Lys|Tyr|Lys|Gly|
| | |435| | | | |440| | | | |445| | | |
|Tyr|Gln|Val|Pro|Pro|Ala|Glu|Leu|Glu|Ser|Val|Leu|Leu|Gln|His|Pro|
| |450| | | | |455| | | | |460| | | | |
|Asn|Ile|Phe|Asp|Ala|Gly|Val|Ala|Gly|Val|Pro|Asp|Pro|Ile|Ala|Gly|
|465| | | | |470| | | | |475| | | | |480|
|Glu|Leu|Pro|Gly|Ala|Val|Val|Val|Leu|Glu|Lys|Gly|Lys|Ser|Met|Thr|
| | | | |485| | | | |490| | | | |495| |
|Glu|Lys|Glu|Val|Met|Asp|Tyr|Val|Ala|Ser|Gln|Val|Ser|Asn|Ala|Lys|
| | | |500| | | | |505| | | | |510| | |
|Arg|Leu|Arg|Gly|Gly|Val|Arg|Phe|Val|Asp|Glu|Val|Pro|Lys|Gly|Leu|
| | |515| | | | |520| | | | |525| | | |
|Thr|Gly|Lys|Ile|Asp|Gly|Lys|Ala|Ile|Arg|Glu|Ile|Leu|Lys|Lys|Pro|
| |530| | | | |535| | | | |540| | | | |
|Val|Ala|Lys|Met| | | | | | | | | | | | |
|545| | | | | | | | | | | | | | | |

( 2 ) INFORMATION FOR SEQ ID NO:3:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA
            oligonucleotide SLF69"

( x i ) SEQUENCE DESCRIPTION: SEQ ID NO:3:

```
ATGGCATTTT CATTACGTTC TATTCTTGAA GCTCAAAAAA TGGAATTACG TAACACTCCA          60

GGAGGTAGTC TCGAGGCTAC AATTG                                               85
```

( 2 ) INFORMATION FOR SEQ ID NO:4:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA
            oligonucleotide SLF70"

( x i ) SEQUENCE DESCRIPTION: SEQ ID NO:4:

CAATTGTAGC CTCGAGACTA CCTCCTGGAG TGTTACGTAA TTCCATTTTT TGAGCTTCAA 60

GAATAGAACG TAATGAAAAT GCCAT 85

( 2 ) INFORMATION FOR SEQ ID NO:5:

( i ) SEQUENCE CHARACTERISTICS:
        ( A ) LENGTH: 1704 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1704

( i x ) FEATURE:
        ( A ) NAME/KEY: misc_feature
        ( B ) LOCATION: 1..1704
        ( D ) OTHER INFORMATION: /note= "Nucleotide sequence of the
        biotinylated firefly luciferase gene contained in
        recombinant plasmid pHLf203 DNA"

( x i ) SEQUENCE DESCRIPTION: SEQ ID NO:5:

```
ATG  GCA  TTT  TCA  TTA  CGT  TCT  ATT  CTT  GAA  GCT  CAA  AAA  ATG  GAA  TTA    48
Met  Ala  Phe  Ser  Leu  Arg  Ser  Ile  Leu  Glu  Ala  Gln  Lys  Met  Glu  Leu
 1                    5                        10                       15

CGT  AAC  ACT  CCA  GGA  GGT  AGT  CTC  GAG  AAC  GAT  GAA  AAT  ATT  GTG  TAT    96
Arg  Asn  Thr  Pro  Gly  Gly  Ser  Leu  Glu  Asn  Asp  Glu  Asn  Ile  Val  Tyr
               20                        25                       30

GGT  CCT  GAA  CCA  TTT  TAC  CCT  ATT  GAA  GAG  GGA  TCT  GCT  GGA  GCA  CAA   144
Gly  Pro  Glu  Pro  Phe  Tyr  Pro  Ile  Glu  Glu  Gly  Ser  Ala  Gly  Ala  Gln
          35                             40                  45

TTG  CGC  AAG  TAT  ATG  GAT  CGA  TAT  GCA  AAA  CTT  GGA  GCA  ATT  GCT  TTT   192
Leu  Arg  Lys  Tyr  Met  Asp  Arg  Tyr  Ala  Lys  Leu  Gly  Ala  Ile  Ala  Phe
     50                        55                       60

ACT  AAC  GCA  CTT  ACC  GGT  GTC  GAT  TAT  ACG  TAC  GCC  GAA  TAC  TTA  GAA   240
Thr  Asn  Ala  Leu  Thr  Gly  Val  Asp  Tyr  Thr  Tyr  Ala  Glu  Tyr  Leu  Glu
65                        70                       75                       80

AAA  TCA  TGC  TGT  CTA  GGA  GAG  GCT  TTA  AAG  AAT  TAT  GGT  TTG  GTT  GTT   288
Lys  Ser  Cys  Cys  Leu  Gly  Glu  Ala  Leu  Lys  Asn  Tyr  Gly  Leu  Val  Val
                    85                            90                      95

GAT  GGA  AGA  ATT  GCG  TTA  TGC  AGT  GAA  AAC  TGT  GAA  GAG  TTC  TTT  ATT   336
Asp  Gly  Arg  Ile  Ala  Leu  Cys  Ser  Glu  Asn  Cys  Glu  Glu  Phe  Phe  Ile
                    100                       105                  110

CCT  GTA  TTA  GCC  GGT  TTA  TTT  ATA  GGT  GTC  GGT  GTG  GCT  CCA  ACT  AAT   384
Pro  Val  Leu  Ala  Gly  Leu  Phe  Ile  Gly  Val  Gly  Val  Ala  Pro  Thr  Asn
               115                       120                  125

GAG  ATT  TAC  ACT  CTA  CGT  GAA  TTG  GTT  CAC  AGT  TTA  GGC  ATC  TCT  AAG   432
Glu  Ile  Tyr  Thr  Leu  Arg  Glu  Leu  Val  His  Ser  Leu  Gly  Ile  Ser  Lys
     130                       135                       140

CCA  ACA  ATT  GTA  TTT  AGT  TCT  AAA  AAA  GGA  TTA  GAT  AAA  GTT  ATA  ACT   480
Pro  Thr  Ile  Val  Phe  Ser  Ser  Lys  Lys  Gly  Leu  Asp  Lys  Val  Ile  Thr
145                       150                       155                  160

GTA  CAA  AAA  ACG  GTA  ACT  GCT  ATT  AAA  ACC  ATT  GTT  ATA  TTG  GAC  AGC   528
Val  Gln  Lys  Thr  Val  Thr  Ala  Ile  Lys  Thr  Ile  Val  Ile  Leu  Asp  Ser
                    165                       170                  175

AAA  GTG  GAT  TAT  AGA  GGT  TAT  CAA  TCC  ATG  GAC  AAC  TTT  ATT  AAA  AAA   576
Lys  Val  Asp  Tyr  Arg  Gly  Tyr  Gln  Ser  Met  Asp  Asn  Phe  Ile  Lys  Lys
               180                       185                  190

AAC  ACT  CCA  CAA  GGT  TTC  AAA  GGA  TCA  AGT  TTT  AAA  ACT  GTA  GAA  GTT   624
Asn  Thr  Pro  Gln  Gly  Phe  Lys  Gly  Ser  Ser  Phe  Lys  Thr  Val  Glu  Val
```

|     |     |     |     |     | 195 |     |     |     | 200 |     |     |     |     | 205 |     |     |      |
|-----|-----|-----|-----|-----|-----|-----|-----|-----|-----|-----|-----|-----|-----|-----|-----|-----|------|
| AAC | CGC | AAA | GAA | CAA | GTT | GCT | CTT | ATA | ATG | AAC | TCT | TCG | GGT | TCA | ACC |     | 672  |
| Asn | Arg | Lys | Glu | Gln | Val | Ala | Leu | Ile | Met | Asn | Ser | Ser | Gly | Ser | Thr |     |      |
|     | 210 |     |     |     | 215 |     |     |     | 220 |     |     |     |     |     |     |     |      |
| GGT | TTG | CCA | AAA | GGT | GTG | CAA | CTT | ACT | CAT | GAA | AAT | TTG | GTC | ACG | CGT |     | 720  |
| Gly | Leu | Pro | Lys | Gly | Val | Gln | Leu | Thr | His | Glu | Asn | Leu | Val | Thr | Arg |     |      |
| 225 |     |     |     |     | 230 |     |     |     | 235 |     |     |     |     |     | 240 |     |      |
| TTT | TCT | CAC | GCT | AGA | GAT | CCA | ATT | TAT | GGA | AAC | CAA | GTT | TCA | CCA | GGC |     | 768  |
| Phe | Ser | His | Ala | Arg | Asp | Pro | Ile | Tyr | Gly | Asn | Gln | Val | Ser | Pro | Gly |     |      |
|     |     |     |     | 245 |     |     |     |     | 250 |     |     |     |     | 255 |     |     |      |
| ACG | GCT | ATT | TTA | ACT | GTA | GTA | CCA | TTC | CAT | CAT | GGT | TTT | GGT | ATG | TTT |     | 816  |
| Thr | Ala | Ile | Leu | Thr | Val | Val | Pro | Phe | His | His | Gly | Phe | Gly | Met | Phe |     |      |
|     |     |     | 260 |     |     |     |     | 265 |     |     |     |     | 270 |     |     |     |      |
| ACT | ACT | TTA | GGC | TAT | CTA | ACT | TGT | GGT | TTT | CGT | ATT | GTC | ATG | TTA | ACG |     | 864  |
| Thr | Thr | Leu | Gly | Tyr | Leu | Thr | Cys | Gly | Phe | Arg | Ile | Val | Met | Leu | Thr |     |      |
|     |     | 275 |     |     |     |     | 280 |     |     |     |     | 285 |     |     |     |     |      |
| AAA | TTT | GAC | GAA | GAG | ACT | TTT | TTA | AAA | ACA | CTG | CAA | GAT | TAC | AAA | TGT |     | 912  |
| Lys | Phe | Asp | Glu | Glu | Thr | Phe | Leu | Lys | Thr | Leu | Gln | Asp | Tyr | Lys | Cys |     |      |
|     | 290 |     |     |     |     | 295 |     |     |     | 300 |     |     |     |     |     |     |      |
| TCA | AGC | GTT | ATT | CTT | GTA | CCG | ACT | TTG | TTT | GCA | ATT | CTT | AAT | AGA | AGT |     | 960  |
| Ser | Ser | Val | Ile | Leu | Val | Pro | Thr | Leu | Phe | Ala | Ile | Leu | Asn | Arg | Ser |     |      |
| 305 |     |     |     |     | 310 |     |     |     | 315 |     |     |     |     |     | 320 |     |      |
| GAA | TTA | CTC | GAT | AAA | TAT | GAT | TTA | TCA | AAT | TTA | GTT | GAA | ATT | GCA | TCT |     | 1008 |
| Glu | Leu | Leu | Asp | Lys | Tyr | Asp | Leu | Ser | Asn | Leu | Val | Glu | Ile | Ala | Ser |     |      |
|     |     |     |     | 325 |     |     |     |     | 330 |     |     |     |     | 335 |     |     |      |
| GGC | GGA | GCA | CCT | TTA | TCT | AAA | GAA | ATT | GGT | GAA | GCT | GTT | GCT | AGA | CGT |     | 1056 |
| Gly | Gly | Ala | Pro | Leu | Ser | Lys | Glu | Ile | Gly | Glu | Ala | Val | Ala | Arg | Arg |     |      |
|     |     |     | 340 |     |     |     |     | 345 |     |     |     |     | 350 |     |     |     |      |
| TTT | AAT | TTA | CCG | GGT | GTT | CGT | CAA | GGC | TAT | GGT | TTA | ACA | GAA | ACA | ACC |     | 1104 |
| Phe | Asn | Leu | Pro | Gly | Val | Arg | Gln | Gly | Tyr | Gly | Leu | Thr | Glu | Thr | Thr |     |      |
|     |     | 355 |     |     |     |     | 360 |     |     |     |     | 365 |     |     |     |     |      |
| TCT | GCA | ATT | ATT | ATC | ACA | CCG | GAA | GGC | GAT | GAT | AAA | CCA | GGT | GCT | TCT |     | 1152 |
| Ser | Ala | Ile | Ile | Ile | Thr | Pro | Glu | Gly | Asp | Asp | Lys | Pro | Gly | Ala | Ser |     |      |
|     |     | 370 |     |     |     |     | 375 |     |     |     |     | 380 |     |     |     |     |      |
| GGC | AAA | GTT | GTG | CCA | TTA | TTT | AAA | GCA | AAA | GTT | ATC | GAT | CTT | GAT | ACT |     | 1200 |
| Gly | Lys | Val | Val | Pro | Leu | Phe | Lys | Ala | Lys | Val | Ile | Asp | Leu | Asp | Thr |     |      |
| 385 |     |     |     |     | 390 |     |     |     | 395 |     |     |     |     |     | 400 |     |      |
| AAA | AAA | ACT | TTG | GGC | CCG | AAC | AGA | CGT | GGA | GAA | GTT | TGT | GTA | AAG | GGT |     | 1248 |
| Lys | Lys | Thr | Leu | Gly | Pro | Asn | Arg | Arg | Gly | Glu | Val | Cys | Val | Lys | Gly |     |      |
|     |     |     |     | 405 |     |     |     |     | 410 |     |     |     |     | 415 |     |     |      |
| CCT | ATG | CTT | ATG | AAA | GGT | TAT | GTA | GAT | AAT | CCA | GAA | GCA | ACA | AGA | GAA |     | 1296 |
| Pro | Met | Leu | Met | Lys | Gly | Tyr | Val | Asp | Asn | Pro | Glu | Ala | Thr | Arg | Glu |     |      |
|     |     |     | 420 |     |     |     |     | 425 |     |     |     |     | 430 |     |     |     |      |
| ATC | ATA | GAT | GAA | GAA | GGT | TGG | TTG | CAC | ACA | GGA | GAT | ATT | GGG | TAT | TAC |     | 1344 |
| Ile | Ile | Asp | Glu | Glu | Gly | Trp | Leu | His | Thr | Gly | Asp | Ile | Gly | Tyr | Tyr |     |      |
|     |     | 435 |     |     |     |     | 440 |     |     |     |     | 445 |     |     |     |     |      |
| GAT | GAA | GAA | AAA | CAT | TTC | TTT | ATC | GTG | GAT | CGT | TTG | AAG | TCT | TTA | ATC |     | 1392 |
| Asp | Glu | Glu | Lys | His | Phe | Phe | Ile | Val | Asp | Arg | Leu | Lys | Ser | Leu | Ile |     |      |
| 450 |     |     |     |     | 455 |     |     |     | 460 |     |     |     |     |     |     |     |      |
| AAA | TAC | AAA | GGA | TAT | CAA | GTA | CCA | CCT | GCT | GAA | TTA | GAA | TCT | GTT | CTT |     | 1440 |
| Lys | Tyr | Lys | Gly | Tyr | Gln | Val | Pro | Pro | Ala | Glu | Leu | Glu | Ser | Val | Leu |     |      |
| 465 |     |     |     |     | 470 |     |     |     | 475 |     |     |     |     |     | 480 |     |      |
| TTG | CAA | CAT | CCA | AAT | ATT | TTT | GAT | GCC | GGC | GTT | GCT | GGC | GTT | CCA | GAT |     | 1488 |
| Leu | Gln | His | Pro | Asn | Ile | Phe | Asp | Ala | Gly | Val | Ala | Gly | Val | Pro | Asp |     |      |
|     |     |     |     | 485 |     |     |     |     | 490 |     |     |     |     | 495 |     |     |      |
| CCT | ATA | GCT | GGT | GAG | CTT | CCG | GGA | GCT | GTT | GTT | GTA | CTT | GAA | AAA | GGA |     | 1536 |
| Pro | Ile | Ala | Gly | Glu | Leu | Pro | Gly | Ala | Val | Val | Val | Leu | Glu | Lys | Gly |     |      |
|     |     |     | 500 |     |     |     |     | 505 |     |     |     |     | 510 |     |     |     |      |
| AAA | TCT | ATG | ACT | GAA | AAA | GAA | GTA | ATG | GAT | TAC | GTT | GCT | AGT | CAA | GTT |     | 1584 |
| Lys | Ser | Met | Thr | Glu | Lys | Glu | Val | Met | Asp | Tyr | Val | Ala | Ser | Gln | Val |     |      |

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 515 |     |     |     | 520 |     |     |     | 525 |     |     |     |      |
| TCA | AAT | GCA | AAA | CGT | TTG | CGT | GGT | GGT | GTC | CGT | TTT | GTG | GAC | GAA | GTA  | 1632 |
| Ser | Asn | Ala | Lys | Arg | Leu | Arg | Gly | Gly | Val | Arg | Phe | Val | Asp | Glu | Val  |
|     | 530 |     |     |     | 535 |     |     |     |     |     | 540 |     |     |     |      |
| CCT | AAA | GGT | CTC | ACT | GGT | AAA | ATT | GAC | GGT | AAA | GCA | ATT | AGA | GAA | ATA  | 1680 |
| Pro | Lys | Gly | Leu | Thr | Gly | Lys | Ile | Asp | Gly | Lys | Ala | Ile | Arg | Glu | Ile  |
| 545 |     |     |     |     | 550 |     |     |     |     | 555 |     |     |     |     | 560  |
| CTG | AAG | AAA | CCA | GTT | GCT | AAG | ATG |     |     |     |     |     |     |     |      | 1704 |
| Leu | Lys | Lys | Pro | Val | Ala | Lys | Met |     |     |     |     |     |     |     |      |
|     |     |     |     | 565 |     |     |     |     |     |     |     |     |     |     |      |

( 2 ) INFORMATION FOR SEQ ID NO:6:

( i ) SEQUENCE CHARACTERISTICS:
        ( A ) LENGTH: 568 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Ala | Phe | Ser | Leu | Arg | Ser | Ile | Leu | Glu | Ala | Gln | Lys | Met | Glu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Asn | Thr | Pro | Gly | Gly | Ser | Leu | Glu | Asn | Asp | Glu | Asn | Ile | Val | Tyr |
|     |     |     | 20  |     |     |     |     | 25  |     |     |     |     | 30  |     |     |
| Gly | Pro | Glu | Pro | Phe | Tyr | Pro | Ile | Glu | Glu | Gly | Ser | Ala | Gly | Ala | Gln |
|     |     |     | 35  |     |     |     | 40  |     |     |     |     | 45  |     |     |     |
| Leu | Arg | Lys | Tyr | Met | Asp | Arg | Tyr | Ala | Lys | Leu | Gly | Ala | Ile | Ala | Phe |
|     |     | 50  |     |     |     | 55  |     |     |     |     | 60  |     |     |     |     |
| Thr | Asn | Ala | Leu | Thr | Gly | Val | Asp | Tyr | Thr | Tyr | Ala | Glu | Tyr | Leu | Glu |
| 65  |     |     |     |     | 70  |     |     |     |     | 75  |     |     |     |     | 80  |
| Lys | Ser | Cys | Cys | Leu | Gly | Glu | Ala | Leu | Lys | Asn | Tyr | Gly | Leu | Val | Val |
|     |     |     |     | 85  |     |     |     |     | 90  |     |     |     |     | 95  |     |
| Asp | Gly | Arg | Ile | Ala | Leu | Cys | Ser | Glu | Asn | Cys | Glu | Glu | Phe | Phe | Ile |
|     |     |     | 100 |     |     |     |     | 105 |     |     |     |     | 110 |     |     |
| Pro | Val | Leu | Ala | Gly | Leu | Phe | Ile | Gly | Val | Gly | Val | Ala | Pro | Thr | Asn |
|     |     |     | 115 |     |     |     |     | 120 |     |     |     |     | 125 |     |     |
| Glu | Ile | Tyr | Thr | Leu | Arg | Glu | Leu | Val | His | Ser | Leu | Gly | Ile | Ser | Lys |
|     |     |     | 130 |     |     |     |     | 135 |     |     |     |     | 140 |     |     |
| Pro | Thr | Ile | Val | Phe | Ser | Ser | Lys | Lys | Gly | Leu | Asp | Lys | Val | Ile | Thr |
| 145 |     |     |     |     | 150 |     |     |     |     | 155 |     |     |     |     | 160 |
| Val | Gln | Lys | Thr | Val | Thr | Ala | Ile | Lys | Thr | Ile | Val | Ile | Leu | Asp | Ser |
|     |     |     |     | 165 |     |     |     |     | 170 |     |     |     |     | 175 |     |
| Lys | Val | Asp | Tyr | Arg | Gly | Tyr | Gln | Ser | Met | Asp | Asn | Phe | Ile | Lys | Lys |
|     |     |     |     | 180 |     |     |     |     | 185 |     |     |     |     | 190 |     |
| Asn | Thr | Pro | Gln | Gly | Phe | Lys | Gly | Ser | Ser | Phe | Lys | Thr | Val | Glu | Val |
|     |     |     | 195 |     |     |     |     | 200 |     |     |     |     | 205 |     |     |
| Asn | Arg | Lys | Glu | Gln | Val | Ala | Leu | Ile | Met | Asn | Ser | Ser | Gly | Ser | Thr |
|     |     | 210 |     |     |     |     | 215 |     |     |     |     | 220 |     |     |     |
| Gly | Leu | Pro | Lys | Gly | Val | Gln | Leu | Thr | His | Glu | Asn | Leu | Val | Thr | Arg |
| 225 |     |     |     |     | 230 |     |     |     |     | 235 |     |     |     |     | 240 |
| Phe | Ser | His | Ala | Arg | Asp | Pro | Ile | Tyr | Gly | Asn | Gln | Val | Ser | Pro | Gly |
|     |     |     |     | 245 |     |     |     |     | 250 |     |     |     |     | 255 |     |
| Thr | Ala | Ile | Leu | Thr | Val | Val | Pro | Phe | His | His | Gly | Phe | Gly | Met | Phe |
|     |     |     |     | 260 |     |     |     |     | 265 |     |     |     |     | 270 |     |
| Thr | Thr | Leu | Gly | Tyr | Leu | Thr | Cys | Gly | Phe | Arg | Ile | Val | Met | Leu | Thr |
|     |     |     | 275 |     |     |     |     | 280 |     |     |     |     | 285 |     |     |

| | | | | | | | | | | | | | | |
|---|---|---|---|---|---|---|---|---|---|---|---|---|---|---|
| Lys | Phe 290 | Asp | Glu | Glu | Thr | Phe 295 | Leu | Lys | Thr | Leu | Gln 300 | Asp | Tyr | Lys | Cys |
| Ser 305 | Ser | Val | Ile | Leu | Val 310 | Pro | Thr | Leu | Phe | Ala 315 | Ile | Leu | Asn | Arg | Ser 320 |
| Glu | Leu | Leu | Asp | Lys 325 | Tyr | Asp | Leu | Ser | Asn 330 | Leu | Val | Glu | Ile | Ala 335 | Ser |
| Gly | Gly | Ala | Pro 340 | Leu | Ser | Lys | Glu | Ile 345 | Gly | Glu | Ala | Val | Ala 350 | Arg | Arg |
| Phe | Asn | Leu 355 | Pro | Gly | Val | Arg | Gln 360 | Gly | Tyr | Gly | Leu | Thr 365 | Glu | Thr | Thr |
| Ser | Ala 370 | Ile | Ile | Ile | Thr | Pro 375 | Glu | Gly | Asp | Asp | Lys 380 | Pro | Gly | Ala | Ser |
| Gly 385 | Lys | Val | Val | Pro | Leu 390 | Phe | Lys | Ala | Lys | Val 395 | Ile | Asp | Leu | Asp | Thr 400 |
| Lys | Lys | Thr | Leu | Gly 405 | Pro | Asn | Arg | Arg | Gly 410 | Glu | Val | Cys | Val | Lys 415 | Gly |
| Pro | Met | Leu | Met 420 | Lys | Gly | Tyr | Val | Asp 425 | Asn | Pro | Glu | Ala | Thr 430 | Arg | Glu |
| Ile | Ile | Asp 435 | Glu | Glu | Gly | Trp | Leu 440 | His | Thr | Gly | Asp | Ile 445 | Gly | Tyr | Tyr |
| Asp | Glu 450 | Glu | Lys | His | Phe | Phe 455 | Ile | Val | Asp | Arg | Leu 460 | Lys | Ser | Leu | Ile |
| Lys 465 | Tyr | Lys | Gly | Tyr | Gln 470 | Val | Pro | Pro | Ala | Glu 475 | Leu | Glu | Ser | Val | Leu 480 |
| Leu | Gln | His | Pro | Asn 485 | Ile | Phe | Asp | Ala | Gly 490 | Val | Ala | Gly | Val | Pro 495 | Asp |
| Pro | Ile | Ala | Gly 500 | Glu | Leu | Pro | Gly | Ala 505 | Val | Val | Leu | Glu 510 | Lys | Gly |
| Lys | Ser | Met 515 | Thr | Glu | Lys | Glu | Val 520 | Met | Asp | Tyr | Val | Ala 525 | Ser | Gln | Val |
| Ser | Asn 530 | Ala | Lys | Arg | Leu | Arg 535 | Gly | Gly | Val | Arg | Phe 540 | Val | Asp | Glu | Val |
| Pro 545 | Lys | Gly | Leu | Thr | Gly 550 | Lys | Ile | Asp | Gly | Lys 555 | Ala | Ile | Arg | Glu | Ile 560 |
| Leu | Lys | Lys | Pro | Val 565 | Ala | Lys | Met | | | | | | | | |

( 2 ) INFORMATION FOR SEQ ID NO:7:

( i ) SEQUENCE CHARACTERISTICS:
        ( A ) LENGTH: 87 amino acids
        ( B ) TYPE: amino acid
        ( C ) STRANDEDNESS: single
        ( D ) TOPOLOGY: unknown ( i i ) MOLECULE TYPE: peptide ( v i ) ORIGINAL SOURCE:
        ( A ) ORGANISM: E. coli ( i x ) FEATURE:
        ( A ) NAME/KEY: Modified-site
        ( B ) LOCATION: 53
        ( D ) OTHER INFORMATION: /product="Lys-53"
            / note= "Lys-53 is biotinylated by the action of biotin
            holoenzyme synthetase"

( x i ) SEQUENCE DESCRIPTION: SEQ ID NO:7:

| | | | | | | | | | | | | | | |
|---|---|---|---|---|---|---|---|---|---|---|---|---|---|---|
| Met 1 | Glu | Ala | Pro | Ala 5 | Ala | Ala | Glu | Ile | Ser 10 | Gly | His | Ile | Val | Arg 15 | Ser |

```
           Pro  Met  Val  Gly  Thr  Phe  Tyr  Arg  Thr  Pro  Ser  Pro  Asp  Ala  Lys  Ala
                          20                       25                      30

Phe  Ile  Glu  Val  Gly  Gln  Lys  Val  Asn  Val  Gly  Asp  Thr  Leu  Cys  Ile
                          35                       40                      45

Val  Glu  Ala  Met  Lys  Met  Met  Asn  Gln  Ile  Glu  Ala  Asp  Lys  Ser  Gly
                50                          55                      60

Thr  Val  Lys  Ala  Ile  Leu  Val  Glu  Ser  Gly  Gln  Pro  Val  Glu  Phe  Asp
           65                      70                      75                            80

Glu  Pro  Leu  Val  Val  Ile  Glu
                               85
```

( 2 ) INFORMATION FOR SEQ ID NO:8:

( i ) SEQUENCE CHARACTERISTICS:
        ( A ) LENGTH: 1908 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: misc_feature
        ( B ) LOCATION: 1..1908
        ( D ) OTHER INFORMATION: /note= "The nucleotide sequence of
                the biotinylated firefly luciferase gene contained in
                recombinant plasmid pHLf248 DNA"

( i x ) FEATURE:
        ( A ) NAME/KEY: CDS
        ( B ) LOCATION: 1..1908

( x i ) SEQUENCE DESCRIPTION: SEQ ID NO:8:

```
ATG  GAA  AAC  ATG  GAG  AAC  GAT  GAA  AAT  ATT  GTG  TAT  GGT  CCT  GAA  CCA        48
Met  Glu  Asn  Met  Glu  Asn  Asp  Glu  Asn  Ile  Val  Tyr  Gly  Pro  Glu  Pro
570                      575                      580

TTT  TAC  CCT  ATT  GAA  GAG  GGA  TCT  GCT  GGA  GCA  CAA  TTG  CGC  AAG  TAT        96
Phe  Tyr  Pro  Ile  Glu  Glu  Gly  Ser  Ala  Gly  Ala  Gln  Leu  Arg  Lys  Tyr
585                      590                      595                      600

ATG  GAT  CGA  TAT  GCA  AAA  CTT  GGA  GCA  ATT  GCT  TTT  ACT  AAC  GCA  CTT       144
Met  Asp  Arg  Tyr  Ala  Lys  Leu  Gly  Ala  Ile  Ala  Phe  Thr  Asn  Ala  Leu
                    605                      610                      615

ACC  GGT  GTC  GAT  TAT  ACG  TAC  GCC  GAA  TAC  TTA  GAA  AAA  TCA  TGC  TGT       192
Thr  Gly  Val  Asp  Tyr  Thr  Tyr  Ala  Glu  Tyr  Leu  Glu  Lys  Ser  Cys  Cys
                    620                      625                      630

CTA  GGA  GAG  GCT  TTA  AAG  AAT  TAT  GGT  TTG  GTT  GTT  GAT  GGA  AGA  ATT       240
Leu  Gly  Glu  Ala  Leu  Lys  Asn  Tyr  Gly  Leu  Val  Val  Asp  Gly  Arg  Ile
          635                      640                      645

GCG  TTA  TGC  AGT  GAA  AAC  TGT  GAA  GAG  TTC  TTT  ATT  CCT  GTA  TTA  GCC       288
Ala  Leu  Cys  Ser  Glu  Asn  Cys  Glu  Glu  Phe  Phe  Ile  Pro  Val  Leu  Ala
     650                      655                      660

GGT  TTA  TTT  ATA  GGT  GTC  GGT  GTG  GCT  CCA  ACT  AAT  GAG  ATT  TAC  ACT       336
Gly  Leu  Phe  Ile  Gly  Val  Gly  Val  Ala  Pro  Thr  Asn  Glu  Ile  Tyr  Thr
665                      670                      675                      680

CTA  CGT  GAA  TTG  GTT  CAC  AGT  TTA  GGC  ATC  TCT  AAG  CCA  ACA  ATT  GTA       384
Leu  Arg  Glu  Leu  Val  His  Ser  Leu  Gly  Ile  Ser  Lys  Pro  Thr  Ile  Val
                    685                      690                      695

TTT  AGT  TCT  AAA  AAA  GGA  TTA  GAT  AAA  GTT  ATA  ACT  GTA  CAA  AAA  ACG       432
Phe  Ser  Ser  Lys  Lys  Gly  Leu  Asp  Lys  Val  Ile  Thr  Val  Gln  Lys  Thr
               700                      705                      710

GTA  ACT  GCT  ATT  AAA  ACC  ATT  GTT  ATA  TTG  GAC  AGC  AAA  GTG  GAT  TAT       480
Val  Thr  Ala  Ile  Lys  Thr  Ile  Val  Ile  Leu  Asp  Ser  Lys  Val  Asp  Tyr
               715                      720                      725

AGA  GGT  TAT  CAA  TCC  ATG  GAC  AAC  TTT  ATT  AAA  AAA  AAC  ACT  CCA  CAA       528
```

|  |  |  |  |  |  |  |  |  |  |  |  |  |  |  |  |
|---|---|---|---|---|---|---|---|---|---|---|---|---|---|---|---|
| Arg | Gly | Tyr | Gln | Ser | Met | Asp | Asn | Phe | Ile | Lys | Lys | Asn | Thr | Pro | Gln |
|  | 730 |  |  |  | 735 |  |  |  |  | 740 |  |  |  |  |  |
| GGT | TTC | AAA | GGA | TCA | AGT | TTT | AAA | ACT | GTA | GAA | GTT | AAC | CGC | AAA | GAA | 576 |
| Gly | Phe | Lys | Gly | Ser | Ser | Phe | Lys | Thr | Val | Glu | Val | Asn | Arg | Lys | Glu |
| 745 |  |  |  | 750 |  |  |  |  | 755 |  |  |  |  | 760 |  |
| CAA | GTT | GCT | CTT | ATA | ATG | AAC | TCT | TCG | GGT | TCA | ACC | GGT | TTG | CCA | AAA | 624 |
| Gln | Val | Ala | Leu | Ile | Met | Asn | Ser | Ser | Gly | Ser | Thr | Gly | Leu | Pro | Lys |
|  |  |  |  | 765 |  |  |  |  | 770 |  |  |  |  | 775 |  |
| GGT | GTG | CAA | CTT | ACT | CAT | GAA | AAT | TTG | GTC | ACG | CGT | TTT | TCT | CAC | GCT | 672 |
| Gly | Val | Gln | Leu | Thr | His | Glu | Asn | Leu | Val | Thr | Arg | Phe | Ser | His | Ala |
|  |  |  | 780 |  |  |  |  | 785 |  |  |  |  | 790 |  |  |
| AGA | GAT | CCA | ATT | TAT | GGA | AAC | CAA | GTT | TCA | CCA | GGC | ACG | GCT | ATT | TTA | 720 |
| Arg | Asp | Pro | Ile | Tyr | Gly | Asn | Gln | Val | Ser | Pro | Gly | Thr | Ala | Ile | Leu |
|  |  | 795 |  |  |  |  | 800 |  |  |  |  | 805 |  |  |  |
| ACT | GTA | GTA | CCA | TTC | CAT | CAT | GGT | TTT | GGT | ATG | TTT | ACT | ACT | TTA | GGC | 768 |
| Thr | Val | Val | Pro | Phe | His | His | Gly | Phe | Gly | Met | Phe | Thr | Thr | Leu | Gly |
|  | 810 |  |  |  |  | 815 |  |  |  |  | 820 |  |  |  |  |
| TAT | CTA | ACT | TGT | GGT | TTT | CGT | ATT | GTC | ATG | TTA | ACG | AAA | TTT | GAC | GAA | 816 |
| Tyr | Leu | Thr | Cys | Gly | Phe | Arg | Ile | Val | Met | Leu | Thr | Lys | Phe | Asp | Glu |
| 825 |  |  |  |  | 830 |  |  |  |  | 835 |  |  |  |  | 840 |
| GAG | ACT | TTT | TTA | AAA | ACA | CTG | CAA | GAT | TAC | AAA | TGT | TCA | AGC | GTT | ATT | 864 |
| Glu | Thr | Phe | Leu | Lys | Thr | Leu | Gln | Asp | Tyr | Lys | Cys | Ser | Ser | Val | Ile |
|  |  |  |  | 845 |  |  |  |  | 850 |  |  |  |  | 855 |  |
| CTT | GTA | CCG | ACT | TTG | TTT | GCA | ATT | CTT | AAT | AGA | AGT | GAA | TTA | CTC | GAT | 912 |
| Leu | Val | Pro | Thr | Leu | Phe | Ala | Ile | Leu | Asn | Arg | Ser | Glu | Leu | Leu | Asp |
|  |  |  | 860 |  |  |  |  | 865 |  |  |  |  | 870 |  |  |
| AAA | TAT | GAT | TTA | TCA | AAT | TTA | GTT | GAA | ATT | GCA | TCT | GGC | GGA | GCA | CCT | 960 |
| Lys | Tyr | Asp | Leu | Ser | Asn | Leu | Val | Glu | Ile | Ala | Ser | Gly | Gly | Ala | Pro |
|  |  | 875 |  |  |  |  | 880 |  |  |  |  | 885 |  |  |  |
| TTA | TCT | AAA | GAA | ATT | GGT | GAA | GCT | GTT | GCT | AGA | CGT | TTT | AAT | TTA | CCG | 1008 |
| Leu | Ser | Lys | Glu | Ile | Gly | Glu | Ala | Val | Ala | Arg | Arg | Phe | Asn | Leu | Pro |
|  | 890 |  |  |  |  | 895 |  |  |  |  | 900 |  |  |  |  |
| GGT | GTT | CGT | CAA | GGC | TAT | GGT | TTA | ACA | GAA | ACA | ACC | TCT | GCA | ATT | ATT | 1056 |
| Gly | Val | Arg | Gln | Gly | Tyr | Gly | Leu | Thr | Glu | Thr | Thr | Ser | Ala | Ile | Ile |
| 905 |  |  |  |  | 910 |  |  |  |  | 915 |  |  |  |  | 920 |
| ATC | ACA | CCG | GAA | GGC | GAT | GAT | AAA | CCA | GGT | GCT | TCT | GGC | AAA | GTT | GTG | 1104 |
| Ile | Thr | Pro | Glu | Gly | Asp | Asp | Lys | Pro | Gly | Ala | Ser | Gly | Lys | Val | Val |
|  |  |  |  | 925 |  |  |  |  | 930 |  |  |  |  | 935 |  |
| CCA | TTA | TTT | AAA | GCA | AAA | GTT | ATC | GAT | CTT | GAT | ACT | AAA | AAA | ACT | TTG | 1152 |
| Pro | Leu | Phe | Lys | Ala | Lys | Val | Ile | Asp | Leu | Asp | Thr | Lys | Lys | Thr | Leu |
|  |  |  | 940 |  |  |  |  | 945 |  |  |  |  | 950 |  |  |
| GGC | CCG | AAC | AGA | CGT | GGA | GAA | GTT | TGT | GTA | AAG | GGT | CCT | ATG | CTT | ATG | 1200 |
| Gly | Pro | Asn | Arg | Arg | Gly | Glu | Val | Cys | Val | Lys | Gly | Pro | Met | Leu | Met |
|  |  | 955 |  |  |  |  | 960 |  |  |  |  | 965 |  |  |  |
| AAA | GGT | TAT | GTA | GAT | AAT | CCA | GAA | GCA | ACA | AGA | GAA | ATC | ATA | GAT | GAA | 1248 |
| Lys | Gly | Tyr | Val | Asp | Asn | Pro | Glu | Ala | Thr | Arg | Glu | Ile | Ile | Asp | Glu |
|  | 970 |  |  |  |  | 975 |  |  |  |  | 980 |  |  |  |  |
| GAA | GGT | TGG | TTG | CAC | ACA | GGA | GAT | ATT | GGG | TAT | TAC | GAT | GAA | GAA | AAA | 1296 |
| Glu | Gly | Trp | Leu | His | Thr | Gly | Asp | Ile | Gly | Tyr | Tyr | Asp | Glu | Glu | Lys |
| 985 |  |  |  |  | 990 |  |  |  |  | 995 |  |  |  |  | 1000 |
| CAT | TTC | TTT | ATC | GTG | GAT | CGT | TTG | AAG | TCT | TTA | ATC | AAA | TAC | AAA | GGA | 1344 |
| His | Phe | Phe | Ile | Val | Asp | Arg | Leu | Lys | Ser | Leu | Ile | Lys | Tyr | Lys | Gly |
|  |  |  |  | 1005 |  |  |  |  | 1010 |  |  |  |  | 1015 |  |
| TAT | CAA | GTA | CCA | CCT | GCT | GAA | TTA | GAA | TCT | GTT | CTT | TTG | CAA | CAT | CCA | 1392 |
| Tyr | Gln | Val | Pro | Pro | Ala | Glu | Leu | Glu | Ser | Val | Leu | Leu | Gln | His | Pro |
|  |  |  | 1020 |  |  |  |  | 1025 |  |  |  |  | 1030 |  |  |
| AAT | ATT | TTT | GAT | GCC | GGC | GTT | GCT | GGC | GTT | CCA | GAT | CCT | ATA | GCT | GGT | 1440 |
| Asn | Ile | Phe | Asp | Ala | Gly | Val | Ala | Gly | Val | Pro | Asp | Pro | Ile | Ala | Gly |
|  |  | 1035 |  |  |  |  | 1040 |  |  |  |  | 1045 |  |  |  |
| GAG | CTT | CCG | GGA | GCT | GTT | GTT | GTA | CTT | GAA | AAA | GGA | AAA | TCT | ATG | ACT | 1488 |

```
Glu  Leu  Pro  Gly  Ala  Val  Val  Val  Leu  Glu  Lys  Gly  Lys  Ser  Met  Thr
     1050                1055                     1060

GAA  AAA  GAA  GTA  ATG  GAT  TAC  GTT  GCT  AGT  CAA  GTT  TCA  AAT  GCA  AAA         1536
Glu  Lys  Glu  Val  Met  Asp  Tyr  Val  Ala  Ser  Gln  Val  Ser  Asn  Ala  Lys
1065                1070                     1075                     1080

CGT  TTG  CGT  GGT  GGT  GTC  CGT  TTT  GTG  GAC  GAA  GTA  CCT  AAA  GGT  CTC         1584
Arg  Leu  Arg  Gly  Gly  Val  Arg  Phe  Val  Asp  Glu  Val  Pro  Lys  Gly  Leu
                    1085                     1090                     1095

ACT  GGT  AAA  ATT  GAC  GGT  AAA  GCA  ATT  AGA  GAA  ATA  CTG  AAG  AAA  CCA         1632
Thr  Gly  Lys  Ile  Asp  Gly  Lys  Ala  Ile  Arg  Glu  Ile  Leu  Lys  Lys  Pro
                    1100                     1105                     1110

GTT  GCT  AAG  GGA  TCC  ATG  GAA  GCG  CCA  GCA  GCA  GCG  GAA  ATC  AGT  GGT         1680
Val  Ala  Lys  Gly  Ser  Met  Glu  Ala  Pro  Ala  Ala  Ala  Glu  Ile  Ser  Gly
               1115                     1120                     1125

CAC  ATC  GTA  CGT  TCC  CCG  ATG  GTT  GGT  ACT  TTC  TAC  CGC  ACC  CCA  AGC         1728
His  Ile  Val  Arg  Ser  Pro  Met  Val  Gly  Thr  Phe  Tyr  Arg  Thr  Pro  Ser
          1130                     1135                     1140

CCG  GAC  GCA  AAA  GCG  TTC  ATC  GAA  GTG  GGT  CAG  AAA  GTC  AAC  GTG  GGC         1776
Pro  Asp  Ala  Lys  Ala  Phe  Ile  Glu  Val  Gly  Gln  Lys  Val  Asn  Val  Gly
1145                1150                     1155                     1160

GAT  ACC  CTG  TGC  ATC  GTT  GAA  GCC  ATG  AAA  ATG  ATG  AAC  CAG  ATC  GAA         1824
Asp  Thr  Leu  Cys  Ile  Val  Glu  Ala  Met  Lys  Met  Met  Asn  Gln  Ile  Glu
                    1165                     1170                     1175

GCG  GAC  AAA  TCC  GGT  ACC  GTG  AAA  GCA  ATT  CTG  GTC  GAA  AGT  GGA  CAA         1872
Ala  Asp  Lys  Ser  Gly  Thr  Val  Lys  Ala  Ile  Leu  Val  Glu  Ser  Gly  Gln
               1180                     1185                     1190

CCG  GTA  GAA  TTT  GAC  GAG  CCG  CTG  GTC  GTC  ATC  GAG                             1908
Pro  Val  Glu  Phe  Asp  Glu  Pro  Leu  Val  Val  Ile  Glu
          1195                     1200
```

( 2 ) INFORMATION FOR SEQ ID NO:9:

( i ) SEQUENCE CHARACTERISTICS:
        ( A ) LENGTH: 636 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Glu  Asn  Met  Glu  Asn  Asp  Glu  Asn  Ile  Val  Tyr  Gly  Pro  Glu  Pro
  1                 5                    10                      15

Phe  Tyr  Pro  Ile  Glu  Glu  Gly  Ser  Ala  Gly  Ala  Gln  Leu  Arg  Lys  Tyr
               20                    25                      30

Met  Asp  Arg  Tyr  Ala  Lys  Leu  Gly  Ala  Ile  Ala  Phe  Thr  Asn  Ala  Leu
          35                     40                    45

Thr  Gly  Val  Asp  Tyr  Thr  Tyr  Ala  Glu  Tyr  Leu  Glu  Lys  Ser  Cys  Cys
     50                     55                    60

Leu  Gly  Glu  Ala  Leu  Lys  Asn  Tyr  Gly  Leu  Val  Val  Asp  Gly  Arg  Ile
 65                     70                    75                       80

Ala  Leu  Cys  Ser  Glu  Asn  Cys  Glu  Glu  Phe  Phe  Ile  Pro  Val  Leu  Ala
                    85                    90                       95

Gly  Leu  Phe  Ile  Gly  Val  Gly  Val  Ala  Pro  Thr  Asn  Glu  Ile  Tyr  Thr
               100                   105                     110

Leu  Arg  Glu  Leu  Val  His  Ser  Leu  Gly  Ile  Ser  Lys  Pro  Thr  Ile  Val
          115                    120                     125

Phe  Ser  Ser  Lys  Lys  Gly  Leu  Asp  Lys  Val  Ile  Thr  Val  Gln  Lys  Thr
     130                    135                     140

Val  Thr  Ala  Ile  Lys  Thr  Ile  Val  Ile  Leu  Asp  Ser  Lys  Val  Asp  Tyr
145                      150                    155                     160
```

```
Arg  Gly  Tyr  Gln  Ser  Met  Asp  Asn  Phe  Ile  Lys  Lys  Asn  Thr  Pro  Gln
               165                 170                 175

Gly  Phe  Lys  Gly  Ser  Ser  Phe  Lys  Thr  Val  Glu  Val  Asn  Arg  Lys  Glu
               180                 185                 190

Gln  Val  Ala  Leu  Ile  Met  Asn  Ser  Ser  Gly  Ser  Thr  Gly  Leu  Pro  Lys
               195                 200                 205

Gly  Val  Gln  Leu  Thr  His  Glu  Asn  Leu  Val  Thr  Arg  Phe  Ser  His  Ala
     210                 215                 220

Arg  Asp  Pro  Ile  Tyr  Gly  Asn  Gln  Val  Ser  Pro  Gly  Thr  Ala  Ile  Leu
225                      230                 235                           240

Thr  Val  Val  Pro  Phe  His  His  Gly  Phe  Gly  Met  Phe  Thr  Thr  Leu  Gly
               245                 250                 255

Tyr  Leu  Thr  Cys  Gly  Phe  Arg  Ile  Val  Met  Leu  Thr  Lys  Phe  Asp  Glu
               260                 265                 270

Glu  Thr  Phe  Leu  Lys  Thr  Leu  Gln  Asp  Tyr  Lys  Cys  Ser  Ser  Val  Ile
          275                 280                 285

Leu  Val  Pro  Thr  Leu  Phe  Ala  Ile  Leu  Asn  Arg  Ser  Glu  Leu  Leu  Asp
     290                 295                 300

Lys  Tyr  Asp  Leu  Ser  Asn  Leu  Val  Glu  Ile  Ala  Ser  Gly  Gly  Ala  Pro
305                      310                 315                           320

Leu  Ser  Lys  Glu  Ile  Gly  Glu  Ala  Val  Ala  Arg  Arg  Phe  Asn  Leu  Pro
               325                 330                 335

Gly  Val  Arg  Gln  Gly  Tyr  Gly  Leu  Thr  Glu  Thr  Thr  Ser  Ala  Ile  Ile
               340                 345                 350

Ile  Thr  Pro  Glu  Gly  Asp  Asp  Lys  Pro  Gly  Ala  Ser  Gly  Lys  Val  Val
               355                 360                 365

Pro  Leu  Phe  Lys  Ala  Lys  Val  Ile  Asp  Leu  Asp  Thr  Lys  Lys  Thr  Leu
     370                 375                 380

Gly  Pro  Asn  Arg  Arg  Gly  Glu  Val  Cys  Val  Lys  Gly  Pro  Met  Leu  Met
385                      390                 395                           400

Lys  Gly  Tyr  Val  Asp  Asn  Pro  Glu  Ala  Thr  Arg  Glu  Ile  Ile  Asp  Glu
               405                 410                 415

Glu  Gly  Trp  Leu  His  Thr  Gly  Asp  Ile  Gly  Tyr  Tyr  Asp  Glu  Glu  Lys
               420                 425                 430

His  Phe  Phe  Ile  Val  Asp  Arg  Leu  Lys  Ser  Leu  Ile  Lys  Tyr  Lys  Gly
          435                 440                 445

Tyr  Gln  Val  Pro  Pro  Ala  Glu  Leu  Glu  Ser  Val  Leu  Leu  Gln  His  Pro
     450                 455                 460

Asn  Ile  Phe  Asp  Ala  Gly  Val  Ala  Gly  Val  Pro  Asp  Pro  Ile  Ala  Gly
465                      470                 475                           480

Glu  Leu  Pro  Gly  Ala  Val  Val  Val  Leu  Glu  Lys  Gly  Lys  Ser  Met  Thr
               485                 490                 495

Glu  Lys  Glu  Val  Met  Asp  Tyr  Val  Ala  Ser  Gln  Val  Ser  Asn  Ala  Lys
               500                 505                 510

Arg  Leu  Arg  Gly  Gly  Val  Arg  Phe  Val  Asp  Glu  Val  Pro  Lys  Gly  Leu
               515                 520                 525

Thr  Gly  Lys  Ile  Asp  Gly  Lys  Ala  Ile  Arg  Glu  Ile  Leu  Lys  Lys  Pro
     530                 535                 540

Val  Ala  Lys  Gly  Ser  Met  Glu  Ala  Pro  Ala  Ala  Ala  Glu  Ile  Ser  Gly
545                      550                 555                           560

His  Ile  Val  Arg  Ser  Pro  Met  Val  Gly  Thr  Phe  Tyr  Arg  Thr  Pro  Ser
               565                 570                 575

Pro  Asp  Ala  Lys  Ala  Phe  Ile  Glu  Val  Gly  Gln  Lys  Val  Asn  Val  Gly
```

|     |     |     |     |     |     |     | 580 |     |     |     |     | 585 |     |     |     |     | 590 |     |     |
| --- | --- | --- | --- | --- | --- | --- | --- | --- | --- | --- | --- | --- | --- | --- | --- | --- | --- | --- | --- |

Asp Thr Leu Cys Ile Val Glu Ala Met Lys Met Met Asn Gln Ile Glu
            595             600             605

Ala Asp Lys Ser Gly Thr Val Lys Ala Ile Leu Val Glu Ser Gly Gln
    610             615             620

Pro Val Glu Phe Asp Glu Pro Leu Val Val Ile Glu
625             630             635

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:10:

AGGAATAAAG AACTCTTCAC AGTT                                                  24

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:11:

TTCATCGTTC TCGAGGTTTT CCATAGA                                     27

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:12:

CCGGCGACCG TTGGATCCAT GGAAGCG                                     27

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:13:

TTATCCAGCG GATCCACTAG TTTACTCGAT GACGACCAGC GG                    42

( 2 ) INFORMATION FOR SEQ ID NO:14:

( i ) SEQUENCE CHARACTERISTICS:
        ( A ) LENGTH: 26 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( x i ) SEQUENCE DESCRIPTION: SEQ ID NO:14:

TGATTGACAT GGATCCCTTA GCAACT                                                                                        2 6

BIOTINATED FIREFLY LUCIFERASE, A GENE FOR BIOTINATED FIREFLY LUCIFERASE, A RECOMBINANT DNA, A PROCESS FOR PRODUCING BIOTINATED LUCIFERASE AND A BIOLUMINESCENT ANALYSIS METHOD

This is a Division of application Ser. No. 08/460,934 filed on Jun. 5, 1995, pending.

FIELD OF THE INVENTION

The present invention relates to biotinated firefly luciferase, a gene for biotinated firefly luciferase, a recombinant DNA, a process for producing biotinated firefly luciferase and a bioluminescent analysis method using the biotinated firefly luciferase.

BACKGROUND OF THE INVENTION

Conventionally, immunoassays making use of chemically modified biotinated firefly luciferase still keeping 50% or more activity are known (Japanese Patent Application Laid-Open Publication No. 138463/1985).

However, none of the biotinated firefly luciferase of uniform properties can be obtained by chemical modification because the residue to which biotin is bound is not determinable and the number of biotin molecules bound to one luciferase molecule is not constant.

Hence, if firefly luciferase biotinated by chemical modification is employed in bioluminescent analysis, detection sensitivity is not satisfactory, and it is inappropriate to employ the biotinated firefly luciferase obtained by chemical modification in a bioluminescent analysis method where high sensitivity is required.

It is known that in cells biotin is bound by the action of biotin holoenzyme synthetase to biotin enzyme at a conserved Lys residue assumed to be one of the active centers of the enzyme [D. Samols et al., The Journal of Biological Chemistry, 263, 6461 (1988)].

Recently, the presence of a biotinated fusion protein was confirmed among fusion proteins between a target protein and a region containing the biotinated Lys residue of biotin enzyme which were produced by gene manipulation [J. E. Cronal, Jr., The Biological Chemistry, 265, 10327 (1990)].

Promega company produced biotinated firefly luciferase by the above method. That is, gene manipulation was used in their attempt to produce a fusion protein between luciferase derived from North American firefly (*Photinus pyralis*) and 12.5 kDa subunit of a transcarboxylase complex as biotin enzyme from *Proprionibacterium shermanii*. However, the resulting fusion protein was insoluble and little or no active biotinated firefly luciferase was obtained [a pamphlet of PinPoint Xa Protein Purification System available from Promega company].

SUMMARY OF THE INVENTION

Under such circumstances, the object of the present invention is to provide biotinated firefly luciferase free from the above drawbacks, a gene for the biotinated firefly luciferase, a process for producing the biotinated firefly luciferase and a bioluminescent analysis method using said luciferase.

The present invention relates to biotinated firefly luciferase, which comprises a biotinated peptide and firefly luciferase linked therein. The term "biotinated peptide" means a peptide which can be bound to biotin by the action of biotin holoenzyme synthetase.

The present invention further relates to biotinated firefly luciferase having the activity of biotinated firefly luciferase, which comprises an animo acid sequence set forth in Sequence No. 6 or 9 in which one or more amino acids may be added, deleted or replaced.

The present invention further relates to a gene for biotinated firefly luciferase, which comprises a gene coding for a biotinated peptide and a gene for firefly luciferase linked therein.

The present invention further relates to a biotinated firefly luciferase gene, which comprises a firefly luciferase gene and a biotinated peptide gene coding for an amino acid sequence bringing about the activity of a biotinated peptide set forth in Sequence No. 1 or 7 in which one or more amino acids may be added, deleted or replaced.

The present invention further relates to a recombinant DNA, which comprises said biotinated firefly luciferase gene inserted into a vector DNA.

The present invention further relates to a process for producing biotinated firefly luciferase, which comprises culturing a microorganism belonging to the genus Escherichia carrying said recombinant DNA, and then recovering the biotinated firefly luciferase from the culture.

The present invention further relates to a bioluminescent analysis method which comprises using said biotinated firefly luciferase.

The present invention further relates to a bioluminescent analysis method which comprises quantifying a ligand by measuring a biotinated receptor with said biotinated firefly luciferase.

DETAILED DESCRIPTION OF THE INVENTION

Figure 1:
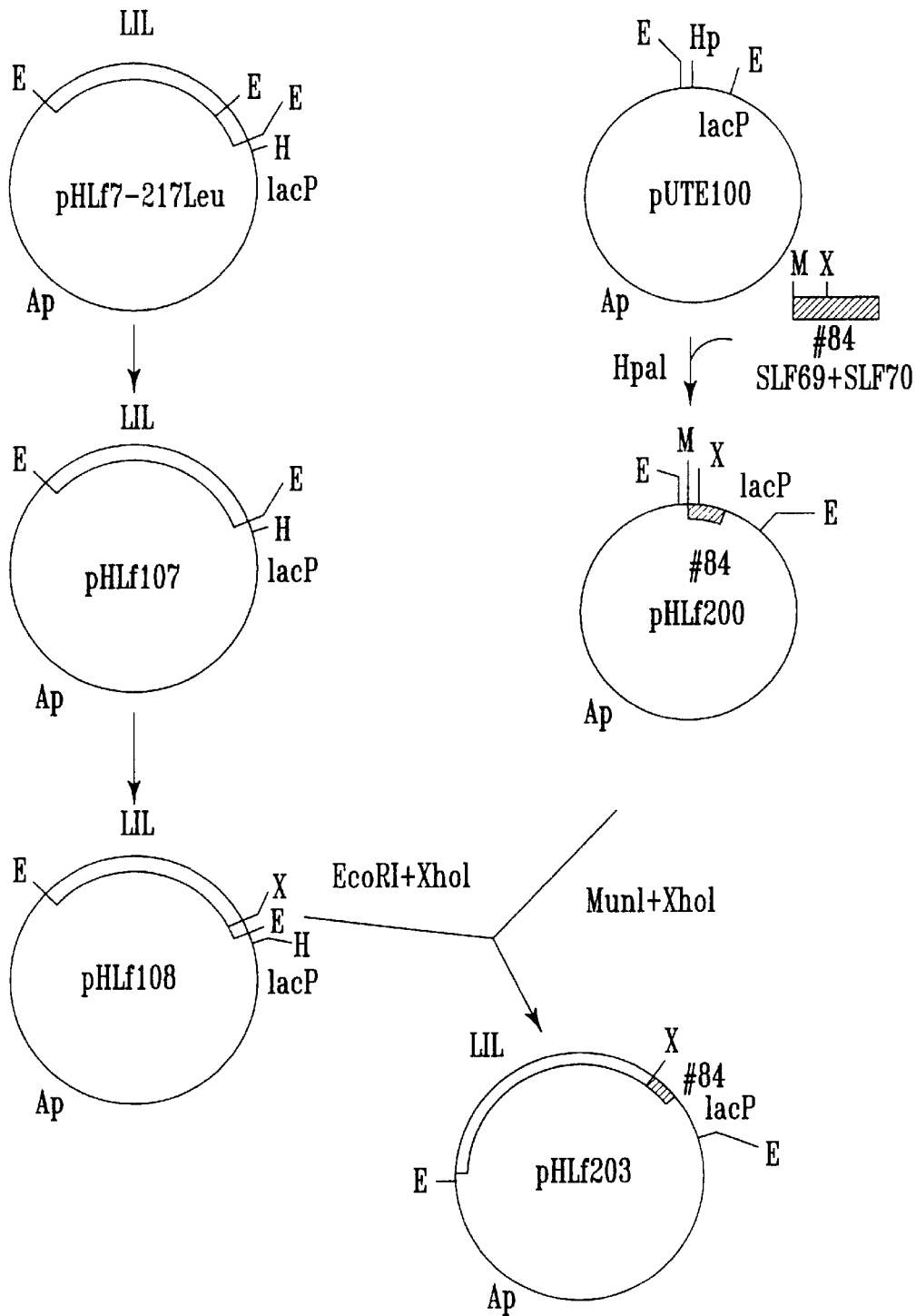
FIG. 1 shows the construction of recombinant plasmid pHLf203 DNA.

As a result of their eager research, the inventors have found that soluble and active biotinated firefly luciferase could be efficiently obtained from the culture of a microorganism belonging to the genus Escherichia carrying a recombinant DNA prepared by inserting into a vector DNA a gene for biotinated firefly luciferase having a biotinated peptide gene coding for an amino acid sequence set forth in Sequence No. 1 or 7 and a firefly luciferase gene linked therein, and also that the biotinated firefly luciferase thus obtained provides a highly sensitive bioluminescent analysis method as compared with chemically modified biotinated firefly luciferase.

Essentially, the present invention involves linking a gene coding for a peptide (biotinated peptide) of from about 10 to about 120 residues to which biotin is bound in cells by the action of biotin holoenzyme synthetase; transforming the resulting gene into a microorganism; and producing a fusion protein in which the biotinated peptide has been biotinated by the action of the biotin holoenzyme synthetase possessed by said microorganism.

In the present invention, the peptide to which biotin is bound in cells by the action of biotin holoenzyme synthetase, i.e. the biotinated peptide, includes e.g. a biotinated lysin residue-containing peptide of 10 to 120 residues from naturally occurring biotin enzyme [e.g. the biotin enzyme described in the Journal of Biological Chemistry, 263, 6461 (1988)] or a biotinated peptide which was artificially created based on such a sequence [e.g. the peptide described in BIO/TECHNOLOGY, 11, 1138 (1993)].

Examples of such biotinated peptides are those of the amino acid sequences of Sequences No. 1 and 7. These peptides can be expected to be subjected without losing their activity to minor modifications of their amino acid sequences. Such modifications of amino acid sequence include the addition, deletion or replacement of one or more amino acids, and those modified peptides which still keep the biotination activity are included in the scope of the biotinated peptides of the invention. Those peptides in which amino acids are added, deleted or replaced can be suitably prepared in a peptide synthetic process known in the art.

As firefly luciferase, mention may be made of luciferase derived from fireflies such as Luciola cruciata, Luciola lateralis (both described by N. Kajiyama et al., Biochim. Biophys. Acta, 1120, 228 (1992), Luciola mingrelica [N. Yu. Philippova and N. N. Ugarova, Biokhimiya, 44, 1508 (1979)] and Photinus pyralis [M. DeLuca and W. D. McElroy, Meth. Enzymol., 72, 3 (1978)]. Among them, the amino acid sequence of thermostable mutant luciferase derived from HEIKE firefly (Luciola lateralis) in which Ala at the 217-position has been replaced by Leu is as shown in Sequence No. 2.

A gene for a biotinated peptide can be synthesized in a DNA synthesizer or can be cloned by the PCR techniques. A gene for firefly luciferase can be cloned by a conventional method [J. Sambrook et al., Molecular Cloning A Laboratory Manual (1989) Cold Spring Harbor Laboratory Press] or by the PCR techniques if the target sequence is known.

The primary sequence of a fusion protein (biotinated firefly luciferase) between a biotinated peptide and firefly luciferase is not limited insofar as the functions of the two peptides are not impaired. That is, either of them may be located at the N-terminal side or one of them may be located within the molecule of the other. A linker sequence such as $(Gly_4Ser)_3$ [J. S. Huston et al., Proc. Natl. Acad. Sci. USA (1988)] or Ser Ser Ala (Asp Asp Ala Lys Lys)$_4$ Asp Gly [M. W. Pantoliano et al., Biochemistry, 30, 10117 (1991)] may also be located between them.

A recombinant can be obtained by linking the gene for biotinated peptide to the gene for firefly luciferase in a conventional method [J. Sambrook et al., Molecular Cloning A Laboratory Manual (1989) Cold Spring Harbor Laboratory Press], ligating the resulting gene for biotinated firefly luciferase in a usual manner to a vector DNA containing a promoter sequence, a marker gene and an origin of replication, and transforming the resulting recombinant DNA into Escherichia coli, yeast (Saccharomyces cerevisiae), etc.

The vector DNA used includes pUC119 (produced by Takara Shuzo Co., Ltd.), pMA56 [G. Ammerer, Meth. Enzymol, 101, 192 (1983)], or the like.

To produce the biotinated firefly luciferase, microorganisms carrying the above recombinant DNA are cultured in a medium to yield a fusion protein in which the conserved Lys residue in the biotinated peptide has been biotinated by the action of biotin holoenzyme synthetase possessed by the microorganisms. The microorganisms may be cultured in either solid or liquid medium, preferably liquid medium.

As the medium, there is employed the one containing at least one inorganic salt such as sodium chloride, potassium dihydrogen phosphate, dipotassium hydrogen phosphate, magnesium sulfate, magnesium chloride, ferric chloride, ferric sulfate, manganese sulfate, etc. and at least one nitrogen source such as yeast extract, trypton, peptone, meat extract, corn steep liquor, exudate of soybean or wheat bran, etc., if necessary a suitable amount of sugars (or carbohydrates), vitamins, etc.

The initial pH of medium is preferably adjusted within pH 7–9. The microorganisms are cultured at 30° to 42° C., preferably around 37° C., for 3 to 24 hours, preferably 5 to 8 hours, by submerged aeration culture, shake culture, or stationary culture.

For recovery of the biotinated firefly luciferase, the culture supernatant and microorganisms are obtained from the culture after incubation, for example by centrifugation, and the microorganisms are disrupted by ultrasonication or treatment with lytic enzyme. Then, the purification of the biotinated firefly luciferase from the culture supernatant or the disrupted cell solution can be effected by a combination of conventional purification means, such as ammonium sulfate precipitation, gel filtration, ion-exchange chromatography, hydrophobic chromatography, etc. The activity of the biotinated firefly luciferase as fusion protein in the cell supernatant or disrupted cell solution can be determined according to the method described by E. A. Bayer et al. [Anal. Biochem., 154, 367 (1986)] and J. R. De Wet et al. [Meth. Enzymol., 133, 3 (1986)].

The biotinated firefly luciferase thus obtained can be applied to a variety of bioluminescent analysis methods. For example, the biotinated firefly luciferase can be bound through the biotin thereof to avidin or streptavidin to form a luciferase complex, and a luminescent analysis method using such a firefly luciferase complex can be applied to a detection system using biotin-avidin in techniques used frequently at present, such as enzyme immunoassays, DNA probe method, immunostaining, receptor measurement, in situ hybridization, etc. [Enzyme Immunoassay (Protein, Nucleic Acid and Enzyme [Tanpakushitsu Kakusan Koso], Extra No. 31 (1987)) compiled by Tsunehiro Kitagawa and published by Kyoritsu Shuppan; Enzyme Immunoassay (1989) written by P. Tijssen and translated by Eiji Ishikawa and published by Tokyo Kagaku Dojin; DNA Probe (1988) written by Toyozo Takahasi and published by CMC].

EXAMPLE

The present invention is described in more detail with reference to the following example.

1. Construction of a plasmid for expression of biotinated firefly luciferase bL203

Two oligonucleotides [SLF69 strand (Sequence No. 3) and complementary SLF70 strand (Sequence No. 4)] coding for biotinated peptide #84 (Met Ala Phe Ser Leu Arg Ser Ile Leu Glu Ala Gln Lys Met Glu Leu Arg Asn Thr Pro Gly Gly Ser) (the Lys residue at the 13-position is assumed to be biotinated by the action of biotin holoenzyme synthetase) [P. J. Shatz, BIO/TECHNOLOGY, 11, 1138 (1993)] and having restriction enzyme XhoI and MunI sites downstream thereof were synthesized in DNA Model 392 synthesizer (manufactured by Applied Biosystems).

1 pmol of each of oligonucleotides SLF69 and SLF70 was phosphorylated with T4 polynucleotide kinase (produced by Takara Shuzo Co., Ltd.) and the two oligonucleotides were annealed at 90° C. for 10 min. and then at 37° C. for 10 min. Separately, plasmid pUTE100 DNA (described in Japanese Patent Application Laid-Open Publication No. 317055/1993) was cleaved with restriction enzyme HpaI and dephosphorylated with alkaline phosphatase (produced Takara Shuzo Co., Ltd.). The cleaved plasmid was ligated to the above annealed oligonucleotide with T4 DNA ligase (produced by Takara Shuzo Co., Ltd.) to give recombinant plasmid pHLf200 DNA having the oligonucleotide coding for biotinated peptide #84 inserted into the HpaI site located downstream from the β-galactosidase promoter in plasmid pUTE100 DNA (see FIG. 1).

Separately, a single-stranded DNA of recombinant plasmid pHLf7-217 Leu [a plasmid prepared by inserting into plasmid pUC119 a gene for thermostable mutant HEIKE firefly luciferase in which Ala at 217-position was replaced by Leu (described in Japanese Patent Application Laid-Open Publication No. 244942/1993), and the amino acid sequence of the thermostable mutant HEIKE firefly luciferase is shown in Sequence No. 2] (SEQ ID NO: 10) was prepared using helper phage M13 K07 (produced by Takara Shuzo Co., Ltd.). The EcoRI site in the luciferase gene was removed using oligonucleotide SLF15 (AGGAATAAAGAACTCTTCACAGTT) and Oligonucleotide-Directed In Vitro Mutagenesis System Version 2 (produced by Amersham) without changing the amino acid sequence of the luciferase gene, whereby plasmid pHLf107 DNA was obtained (see FIG. 1). Using oligonucleotide SLF43 (TTCATCGTTCTCGAGGTTTTCCATAGA) (SEQ ID NO: 11) (restriction enzyme XhoI site is underlined), a XhoI site was introduced in an analogous manner in the neighborhood of the 5'-terminal of the luciferase gene in recombinant pHLf107 DNA, whereby plasmid pHLf108 was obtained (see FIG. 1).

After pHLf108 was cleaved with restriction enzymes XhoI and EcoRI (both produced by Takara Shuzo Co., Ltd.), a luciferase gene fragment was obtained in agarose gel electrophoresis using a gene clean II kit (produced by BIO101). This fragment was ligated to pHLf200 previously cleaved with XhoI and MunI (both produced by Takara Shuzo Co., Ltd.), to give recombinant plasmid pHLf203 DNA which can initiate the expression of biotinated firefly luciferase bL203 by the β-galactosidase promoter (see FIG. 1). The nucleotide sequence of the biotinated firefly luciferase bL203 gene contained in recombinant plasmid pHLf203 DNA is shown in Sequence No. 5 and the amino acid sequence encoded by said gene is shown in Sequence No. 6.

2. Confirmation of the production of biotinated firefly luciferase bL203 in *E. coli*

Recombinant plasmid pHLf203 DNA-containing *E. coli* JM101 [pHLf203] [using *E. coli* JM101 (ATCC33876) as host] (*E. coli* JM101 [pHLf203] has been deposited as FERM BP-5052 with the National Institute of Bioscience and Human-Technology, Agency of Industrial Science and Technology, Japan) was cultured at 30° C. for 5 hours with stirring at 120 r.p.m. in 2 ml of LB medium (1% Bacto-trypton, 0.5% yeast extract, 0.5% sodium chloride) containing 0.2 mM isopropyl-β-thiogalactoside (IPTG) and 50 μg/ml ampicillin. The bacteria were recovered by centrifugation at 5,000 r.p.m. for 5 min., disrupted by ultrasonication and centrifuged at 12,000 r.p.m. for 5 min., to give a supernatant of the disrupted bacteria.

The supernatant of the disrupted bacteria was determined for the activity of biotinated firefly luciferase bL203 in the following manner. Each well in microtiter immunoassay plate FluoroNunc Plate C96 White Maxisorp (manufactured by Nunc), was charged with 100 μl biotinated bovine serum albumin (BSA) solution [10 μg/ml ALBUMIN BOVINE-BIOTIN Labeled (SIGMA), 15 mM sodium carbonate (pH 9.6)], and the plate was allowed to stand at 4° C. for 16 hours to immobilize the biotinated BSA. The biotinated BSA solution was discharged from the well and each well was washed with 300 μl of TPBS [0.05% Tween 20, 65 mM sodium chloride, 10 mM sodium phosphate (pH 7.2)], and then 300 μl blocking solution [1% BSA, 65 mM sodium chloride, 10 mM sodium phosphate (pH 7.2)] was added thereto and allowed to stand at 37° C. for 2 hours to block the well. After the blocking solution was discharged, each well was washed with 300 μl of TPBS, then charged with 100 μl of 10 μg/ml avidin (produced by Wako Junyaku) dissolved in PBS or with an equal volume of PBS as the control, and allowed to stand for 1 hour at room temperature. Each well was washed with TPBS, and 100 μl of a 10-fold dilution in PBS of the above supernatant of the disrupted *E. coli* JM101 [pHLf203] was added thereto and allowed to stand for 1 hour at room temperature. The dilution of the supernatant of the disrupted bacteria was discharged and each well was washed 4 times with 300 μl of TPBS.

The luciferase activity of each well was determined in the following manner. The microtiter immunoassay plate was attached to Microplate Luminometer ML3000 (manufactured by DYNATECH), and 100 μl substrate solution [0.069 mM luciferin (produced by SIGMA), 4 mM ATP, 4.3 mM magnesium chloride, 25 mM glycylglycine (pH 7.8)] was added thereto and the number of photons generated during 20 seconds was determined. The result showed that while the emission in the well to which avidin had not been added was 96 counts, the emission in the well to which avidin had been added was 27,000 counts, indicating the significant increase of the activity of luciferase. Hence, the production of firefly luciferase having the ability to bind to avidin, i.e. active biotinated firefly luciferase bL203 in the supernatant of the disrupted bacteria *E. coli* JM101 [pHLf203] was confirmed.

3. Purification of biotinated firefly luciferase bL203

*E. coli* JM101 [pHLF203] was cultured at 30° C. with stirring at 120 r.p.m. for 5 hours in 1 liter of LB medium (1% Bacto-trypton, 0.5% yeast extract, 0.5% sodium chloride) containing 0.2 mM isopropyl-β-thiogalactoside (IPTG), 50 μg/ml ampicillin and 10 μg/ml D-biotin. The bacteria were recovered by centrifugation at 5,000 r.p.m. for 5 min. and suspended in 100 ml buffer [25 mM tris(hydroxymethyl) aminomethane (Tris), 1 mM ethylenediaminetetraacetic acid (EDTA), 10% saturated ammonium sulfate, 1 mg/ml lysozyme, pH 7.8]. The bacteria were lysed by being frozen and melted 3 times and centrifuged at 12,000 r.p.m. for 5 min. to give a supernatant of the disrupted bacteria solution. The purification of bL203 from the supernatant of the disrupted bacteria solution was conducted according to the method described by Kajiyama et al. [N. Kajiyama et al., Biochim. Biophys. Acta, 1120, 228 (1992)]. The concentration of the purified bL203 was determined by measuring ultraviolet absorption. The specific activity of the purified bL203 was 98% relative to that of the purified thermostable HEIKE firefly luciferase in which Ala at the 217-position was replaced by Leu. The activity of the purified bL203 was not lost even after more than 60-days storage at 4° C.

4. Preparation of chemically modified biotinated firefly luciferase

In order to compare with biotinated firefly luciferase bL203 of the present invention, chemically modified biotinated firefly luciferase was prepared according to the method of Japanese Patent Laid-Open Publication No. 138463/1985. According to the publication, the firefly luciferase used was the firefly luciferase derived from *Photinus pyralis* obtained from Sigma Chemical. To 400 μl of 2.6 mg/ml firefly luciferase in a reaction buffer [0.1M sodium chloride, 0.1M potassium phosphate (pH 7.6)] were added 592 μl of 5.5 μM ATP solution in the same buffer and 60 nmol N-hydroxysuccinimide biotin (produced by Pierce) in 8 μl dimethylsulfoxide. After overnight incubation at 4° C., the sample was dialyzed against a buffer [10% glycerol, 1 mM EDTA, 2 mM β-mercaptoethanol, 0.1M potassium phosphate (pH 7.5)]. The activity of this labeled firefly luciferase was 62% relative to the unmodified firefly luciferase, and the chemically modified firefly luciferase with at least 50% activity was obtained as described in the above publication, but this activity was far from 98% attained by the biotinated firefly luciferase obtained in the method of the present invention.

5. Change in the activity by binding to streptavidin

The change in the activity upon binding to streptavidin was compared between biotinated firefly luciferase bL203 and the chemically modified biotinated firefly luciferase. 0.1 ng/ml of each biotinated firefly luciferase in a luciferase diluent [1% BSA, 1 mM EDTA, 1 mM β-mercaptoethanol, 50 mM HEPES (pH 7.5)] was mixed with an equal volume of 1 μg/ml streptavidin (Boehringer Mannheim GmbH) in the luciferase diluent or with the luciferase diluent as the control and allowed to stand for 30 min. at room temperature. 50 μl of each sample solution was put to a well on Microtiter Plate Microlite 2 (produced by Dynatech Laboratories) which was then attached to a microplate reader LUMINOUS CT-9000D (DIA IATRON) for bioluminescent and chemiluminescent measurements, and 50 μl substrate solution [40 mM ATP, 1.4 mM luciferin, 300 mM magnesium sulfate, 50 mM HEPES (pH 7.5)] was put to each well and the number of photons generated for 10 seconds was determined. The result showed that after mixed with streptavidin, the remaining activities of biotinated firefly luciferase bL203 and the chemically modified biotinated firefly luciferase were 93% and 62%, respectively, indicating that the change of the activity was small in the case of the biotinated firefly luciferase bL203 of the present invention, while nearly 40% of the activity was lost in the case of the chemically modified biotinated firefly luciferase.

6. Sandwich ELISA using biotinated firefly luciferase bL203

100 μl of 5 μg/ml goat anti-mouse IgG Fc fragment-specific polyclonal antibody (produced by Jackson Immuno Research) in 50 mM sodium carbonate buffer (pH 9.6) was put to each well in microtiter plate Microlite 2 and immobilized at 4° C. overnight. Each well was washed 4 times with 300 μl of T-TBS [0.05% Tween 20, 0.15M NaCl, 50 mM Tris (pH 7.6)], then charged with 200 μl of a 4-fold dilution of Blockace (produced by Dainippon Seiyaku) and blocked at 4° C. overnight. The well was washed in the same manner, then charged with 100 μl of 1 pg/ml to 1000 pg/ml mouse IgG$_1$ (produced by Chemicon) in a 4-fold dilution of Blockace or with 100 μl of a 4-fold dilution of Blockace as the negative control and allowed to stand at 37° C. for 2 hours. After washing, 100 μl of 0.1 μg/ml biotinated goat anti-mouse IgG F(ab')$_2$ fragment-specific polyclonal antibody F(ab')$_2$ fragment (produced by Jackson Immuno Research) in a 4-fold dilution of Blockace was added thereto and allowed to stand at 37° C. for 1 hour. After washing, 100 μl of 2 μg/ml streptavidin (Boehringer Mannheim GmbH) in a 4-fold dilution of Blockace was added thereto and allowed to stand at room temperature for 30 min. After washing, 100 μl of 5×10$^{-13}$ mol/ml biotinated firefly luciferase bL203 or the chemically modified biotinated firefly luciferase in the luciferase diluent was added thereto and allowed to stand at room temperature for 30 min. After washing, 50 μl luciferase diluent [1% BSA, 1 mM EDTA, 1 mM β-mercaptoethanol, 50 mM HEPES (pH 7.5)] was put to each well and then the plate was attached to a microplate reader LUMINOUS CT-9000D (DIA IATRON) for bioluminescent and chemiluminescent measurements. 50 μl substrate solution [40 mM ATP, 1.4 mM luciferin, 300 mM magnesium sulfate, 50 mM HEPES (pH 7.5)] was added to each well and the number of photons generated for 10 seconds were determined as shown in Table 1.

TABLE 1

| mouse IgG$_1$ concentration (pg/ml) | emission with biotinated firefly luciferase bL203 (counts)[Note 1] | emission with chemically modified biotinated luciferase (counts)[Note 1] |
| --- | --- | --- |
| 0 | 5633 | 131 |
| 1 | 5773 | 156 |
| 5 | 6906 | 151 |
| 10 | 7781 | 158 |
| 50 | 16319 | 196 |
| 100 | 24950 | 241 |
| 1000 | 162429 | 1117 |

Note [1] mean value of 4 wells measurements

As is evident from Table 1, biotinated firefly luciferase bL203 could be used for measurements from 5 pg/ml (P<0.05) according to the Student's t test [R. C. Canbel: Introduction to Statistics for Biologists (2nd edition) (1976), translated into Japanese by Susumu Ishii and published by Baifukan], while the chemically modified biotinated firefly luciferase could be used for measurements from 50 pg/ml with a significant difference (P<0.05). From the foregoing, it became evident that the biotinated firefly luciferase of the present invention attains 10 times sensitivity as high as the conventional chemically modified biotinated firefly luciferase.

7. Construction of a plasmid for expression of biotinated firefly luciferase bL248

It is known that a biotin carboxyl carrier protein (referred to hereinafter as BCCP) as a subunit of acetyl CoA carboxylase from E. coli is biotinated at the Lys residue at the 122-position by the action of biotin holoenzyme synthetase in E. coli [The Journal of Biological Chemistry, 263, 6461 (1988)]. A gene coding for a biotinated Lys residue-containing polypeptide consisting of 87 residues of the C-terminal side of BCCP (referred to hereinafter as BCCP-87, Sequence No. 7) was cloned in the following manner. According to the method described in Japanese Patent Application Laid-Open Publication No. 292584/1994, genomic DNA was obtained from E. coli 1100 (obtained from Max-Plank-Institute, Heidelberg, Germany) and denatured. On the basis of the nucleotide sequence of the BCCP gene reported by S. Muramatsu et al. [Nucleic Acids Research, 17, 3982 (1989)], oligonucleotide SLF116 (CCGGCGACCGTTGGATCCATGGAAGCG) (SEQ ID NO: 12) as the 5'-terminal primer and oligonucleotide SLF117 (TTATCCAGCGGATCCACTAGTTTACT-CGATGACGACCAGCGG) (SEQ ID NO: 13) as the 3'-terminal primer were synthesized in DNA model 392 synthesizer (manufactured by Applied Biosystems). For subsequent subcloning, restriction enzyme BamHI recognition site (underlined) was introduced to each primer. 1 pmol of each of primer SLF116 and primer SLF117 and 0.1 μg of the above denatured genomic DNA from E. coli were subjected to PCR amplification using DNA Thermal Cycler (produced by Perkin-Elmer) and a GeneAmp PCR reagent kit containing Ampli Taq DNA polymerase (produced by Takara Shuzo Co., Ltd.) to give 1 μg of a gene fragment coding for BCCP-87 which was then digested with BamHI.

Figure 2:
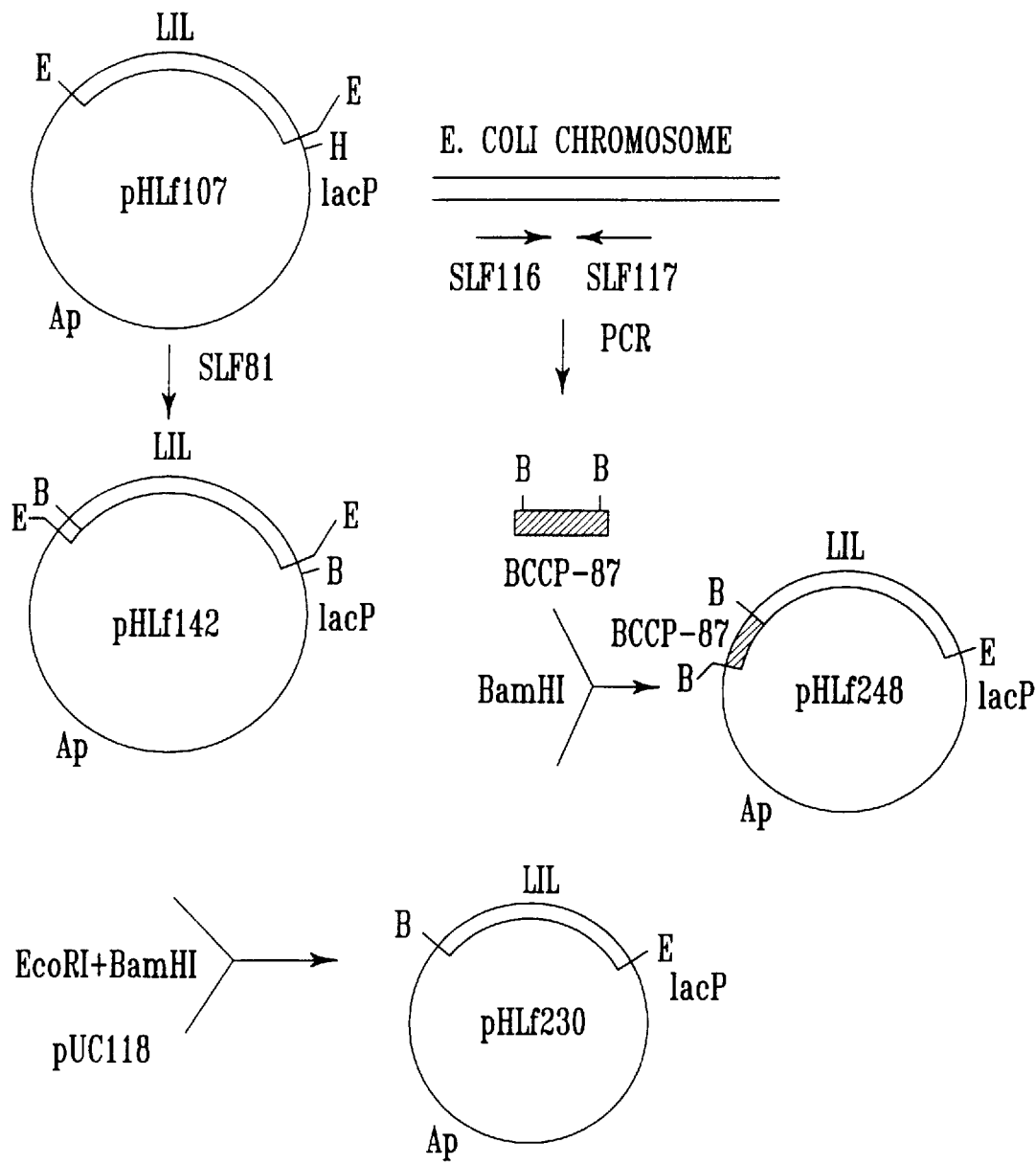
FIG. 2 shows the construction of recombinant plasmid pHLf248 DNA.

Separately, plasmid pHLf142 DNA was obtained in which a BamHI site was introduced in the neighborhood of the 3'-terminal of the luciferase gene in plasmid pHLf107 DNA (see FIG. 1) by site-specific mutation described in item 1 above using oligonucleotide SLF81 (TGATTGACATGGATCCCTTAGCAACT) (SEQ ID NO: 14) (restriction enzyme BamHI site is underlined) (see FIG. 2). Then, plasmid pHLf142 DNA was completely digested with restriction enzymes BamHI and EcoRI (both produced by Takara Shuzo Co., Ltd.) and subjected to agarose gel electrophoresis. Then a luciferase gene fragment was prepared using a gene clean II kit (produced by BIO101). This fragment was ligated to plasmid pUC118 DNA (produced by Takara Shuzo Co., Ltd.) previously cleaved with BamHI and EcORI, whereby plasmid pHLf230 DNA was constructed (see FIG. 2).

Plasmid pHLf230 DNA was cleaved with BamHI and then ligated in a usual manner to the above BamHI-digested BCCP-87 gene fragment, to give recombinant plasmid pHLf248 DNA capable of initiating by the β-galactosidase promoter the expression of biotinated firefly luciferase bL248 having BCCP-87 fused with the C-terminal of thermostable HEIKE firefly luciferase (Sequence No. 2) (see FIG. 2). The nucleotide sequence of the biotinated firefly luciferase bL248 gene contained in recombinant plasmid pHLf248 is shown in Sequence No. 8 and the amino acid sequence encoded by said gene is shown in Sequence No. 9.

8. Confirmation of the production of biotinated firefly luciferase bL248 in *E. coli*

*E. coli* JM101 [pHLf248] carrying recombinant plasmid pHLf248 DNA [using *E. coli* JM101 (ATCC33876) as host] [*E. coli* JM101 [pHLf248] has been deposited as FERM BP-5081 with the National Institute of Bioscience and Human-Technology, Agency of Industrial Science and Technology, Japan] was cultured and the activity of the biotinated luciferase was determined according to the same manner as in item 2 above. The result indicated that while the emission in the well to which avidin had not been added was 75 counts, the emission in the well to which avidin had been added was 11,000 counts, indicating that *E. coli* JM101 [pHLf248] produced active biotinated firefly luciferase bL248.

9. Partial purification of biotinated firefly luciferase bL248

According to the method described in item 3, *E. coli* JM101 [pHLf248] was cultured and a supernatant was obtained from the disrupted microorganism. According to the method described by Kajiyama et al. (N. Kajiyama et al., Biochem. Biophys. Acta, 1120, 228 (1992)), a fraction precipitated in the supernatant between 30–60% saturated ammonium sulfate was obtained and suspended in a buffer (25 mM Tris, 1 mM EDTA, 10% saturated ammonium sulfate, pH 7.8) and this solution was served as crude purified preparation. Biotinated firefly luciferase bL248 upon binding to streptavidin maintained 102% activity as determined according to the method described in item 5 above, indicating that the activity was not lost even after binding to streptavidin.

10. Sandwich ELISA using biotinated firefly luciferase bL248

The above crude enzyme solution of biotinated firefly luciferase bL248 was used for quantification of mouse $IgG_1$ by sandwich ELISA according to the method described in item 6 above (Table 2). The amount of biotinated firefly luciferase bL248 was the same in terms of activity as that of biotinated firefly luciferase bL203 used in item 6. As is evident from Table 2, biotinated firefly luciferase bL248 could be used for measurements from 10 pg/ml ($P<0.05$) according to Student's t test and attained 5 times sensitivity as high as the limit of measurement (50 pg/ml) of the conventional chemically modified biotinated firefly luciferase (Table 1).

TABLE 2

| mouse $IgG_1$ concentration (pg/ml) | emission with biotinated firefly luciferase bL248 (counts)[Note 1] |
|---|---|
| 0 | 379 |
| 1 | 376 |
| 5 | 394 |
| 10 | 458 |
| 50 | 856 |
| 100 | 1393 |
| 1000 | 11219 |

[Note 1] mean value of 4 wells measurements

---

What is claimed is:

1. A gene encoding a fusion protein comprising the amino acid sequence of SEQ ID NO: 6 or 9.

2. The gene of claim 1, which encodes a fusion protein comprising the amino acid sequence of SEQ ID NO: 6.

3. The gene of claim 1, which encodes a fusion protein comprising the amino acid sequence of SEQ ID NO: 9.

4. The gene of claim 1, which encodes a fusion protein consisting of the amino acid sequence of SEQ ID NO: 6.

5. The gene of claim 1, which encodes a fusion protein consisting of the amino acid sequence of SEQ ID NO: 9.

6. The gene of claim 1, wherein the nucleotide sequence of the gene comprises SEQ ID NO: 5.

7. The gene of claim 1, wherein the nucleotide sequence of the gene comprises SEQ ID NO: 8.

8. The gene of claim 1, wherein the nucleotide sequence of the gene consists of SEQ ID NO: 5.

9. The gene of claim 1, wherein the nucleotide sequence of the gene consists of SEQ ID NO: 8.

10. A recombinant DNA vector comprising the gene of claim 1.

11. A recombinant DNA vector comprising the gene of claim 2.

12. A recombinant DNA vector comprising the gene of claim 3.

13. A recombinant DNA vector comprising the gene of claim 4.

14. A recombinant DNA vector comprising the gene of claim 5.

15. A recombinant DNA vector comprising the gene of claim 6.

16. A recombinant DNA vector comprising the gene of claim 7.

17. A recombinant DNA vector comprising the gene of claim 8.

18. A recombinant DNA vector comprising the gene of claim 9.

19. A process for producing a luciferase fusion protein which can be enzymatically biotinated by biotin holoenzyme synthetase and comprises the amino acid sequence of SEQ ID NO: 6 or 9, comprising:

(a) culturing a microorganism belonging to the genus Escherichia comprising the recombinant DNA vector of claim 10 in a culture medium; and (b) recovering the firefly luciferase fusion protein from the culture medium.

20. A process for producing a luciferase fusion protein which can be enzymatically biotinated by biotin holoenzyme synthetase and comprises the amino acid sequence of SEQ ID NO: 6, comprising:

(a) culturing a microorganism belonging to the genus Escherichia comprising the recombinant DNA vector of claim 11 in a culture medium; and (b) recovering the firefly luciferase fusion protein from the culture medium.

21. A process for producing a luciferase fusion protein which can be enzymatically biotinated by biotin holoenzyme synthetase and comprises the amino acid sequence of SEQ ID NO: 9, comprising:

(a) culturing a microorganism belonging to the genus Escherichia comprising the recombinant DNA vector of claim 12 in a culture medium; and (b) recovering the firefly luciferase fusion protein from the culture medium.

* * * * *